United States Patent
Gould (10) Patent No.: US 10,926,039 B2
(45) Date of Patent: Feb. 23, 2021

(54) INJECTION DEVICE WITH SYRINGE CARRIER LOCK

(71) Applicant: Owen Mumford Limited, Oxford (GB)

(72) Inventor: Oliver Gould, Oxford (GB)

(73) Assignee: Owen Mumford Limited, Oxford (GB)

( * ) Notice: Subject to any disclaimer, the term of this patent is extended or adjusted under 35 U.S.C. 154(b) by 437 days.

(21) Appl. No.: 15/570,696

(22) PCT Filed: Apr. 29, 2016

(86) PCT No.: PCT/EP2016/059698
§ 371 (c)(1),
(2) Date: Oct. 30, 2017

(87) PCT Pub. No.: WO2016/174249
PCT Pub. Date: Nov. 3, 2016

(65) Prior Publication Data
US 2018/0289899 A1    Oct. 11, 2018

(30) Foreign Application Priority Data

Apr. 30, 2015    (GB) .................................... 1507489.1

(51) Int. Cl.
*A61M 5/32*    (2006.01)
*A61M 5/20*    (2006.01)
*A61M 5/31*    (2006.01)

(52) U.S. Cl.
CPC ........ *A61M 5/3245* (2013.01); *A61M 5/2033* (2013.01); *A61M 5/3202* (2013.01);
(Continued)

(58) Field of Classification Search
CPC .............. A61M 5/3245; A61M 5/2033; A61M 5/3202; A61M 5/326
(Continued)

(56) References Cited

U.S. PATENT DOCUMENTS

| 8,652,100 B1 | 2/2014 | Cowe |
| 2010/0185178 A1 | 7/2010 | Sharp et al. |

(Continued)

FOREIGN PATENT DOCUMENTS

| EP | 2399631 A1 | 12/2011 |
| EP | 2438941 A1 | 4/2012 |

(Continued)

OTHER PUBLICATIONS

Search Report for GB Application No. 1507489.1, dated Mar. 22, 2016, 3 pages.

(Continued)

*Primary Examiner* — Phillip A Gray
(74) *Attorney, Agent, or Firm* — Quarles & Brady LLP (57) ABSTRACT

An autoinjector device is disclosed which comprises a body portion and a syringe carrier, for supporting a syringe with a needle at its forward end. The syringe carrier is moveably mounted within the housing such that forward movement relative to the housing may extend the needle from a forward end of the body. The syringe carrier has a latch element arranged to cooperate with a corresponding retention feature of the body portion to releasably hold the syringe carrier in a rearward position within the body potion. A delivery mechanism is arranged to forwardly displace the syringe carrier relative to the housing and to deliver a dose of medicament from the syringe. A shroud assembly is provided at a forward end of the device. The shroud further comprises a locking arrangement which blocks releasing movement of the latch element from the retention feature when the shroud is in a first, forward position and is unlocked when the shroud is in a second, rearward position.

16 Claims, 12 Drawing Sheets

(52) U.S. Cl.
CPC ....... *A61M 5/326* (2013.01); *A61M 2005/206* (2013.01); *A61M 2005/208* (2013.01); *A61M 2005/3125* (2013.01); *A61M 2005/3247* (2013.01); *A61M 2005/3263* (2013.01); *A61M 2005/3265* (2013.01)

(58) Field of Classification Search
USPC ........................................................ 604/198
See application file for complete search history.

(56) References Cited

U.S. PATENT DOCUMENTS

2013/0131595 A1* 5/2013 Ekman ................ A61M 5/1452
  604/117
2013/0204195 A1 8/2013 Ekman et al.
2013/0317479 A1* 11/2013 Brereton ............ A61M 5/31511
  604/506

FOREIGN PATENT DOCUMENTS

| | | |
|---|---|---|
| EP | 2468335 A1 | 6/2012 |
| EP | 2583706 A1 | 4/2013 |
| EP | 2698179 A1 | 2/2014 |
| EP | 2716318 A1 | 4/2014 |
| EP | 2823837 A1 | 1/2015 |
| GB | 2424838 A | 10/2006 |
| GB | 2461088 A | 12/2009 |
| WO | WO2010076569 A2 | 7/2010 |
| WO | WO2011012903 A1 | 2/2011 |
| WO | WO2014062488 A1 | 4/2014 |
| WO | WO2014066256 A1 | 5/2014 |

OTHER PUBLICATIONS

International Search Report and Written Opinion for PCT Application No. PCT/EP2016/059698, dated Sep. 30, 2016, 20 pages.

* cited by examiner

SECTION C-C

INJECTION DEVICE WITH SYRINGE CARRIER LOCK

CROSS-REFERENCE TO RELATED APPLICATIONS

This application represents the U.S. National Stage of International Application No. PCT/EP2016/059698 filed on Apr. 29, 2016, which is incorporated by reference in its entirety, and is based upon, claims priority to, and incorporates herein by reference in its entirety, United Kingdom Patent Application Serial No. GB 1507489.1, filed Apr. 30, 2015.

FIELD OF THE INVENTION

The invention relates to injection devices for delivering a dose of medicament from a syringe. In particular, but not exclusively, the invention relates to a shroud arrangement for an injection device.

BACKGROUND OF THE INVENTION

Injection devices are used for the convenient administration of medicaments. For example, injection devices (which may typically be in the form of a pen injector) may be used for providing a single metered dose of a medicament, such as Epinephrine, in an emergency or for providing regular metered doses of a medicament, such as Insulin. Such devices may be either single use "disposable" devices in which the device is typically provided with a syringe already installed, and which is not user-replaceable, or "reusable" devices which allow the user to replace the syringe when the medicament has been used.

It may be noted that whilst the term "syringe" is used herein for clarity and convenience, the skilled person will appreciate that in some arrangements the syringe may be a cartridge (which, for example, may be arranged to receive a disposable needle). In some arrangements the syringe/cartridge/medicament container may formed integrally with the (or part of the) injection device.

Injection devices may be provided in the form of an "autoinjector" device. As used herein an autoinjector is an injector device in which, in addition to automating the delivery of the medicament, the device is also arranged to automate the insertion of a needle into the skin prior to the delivery of the medicament.

Injection devices generally comprise a delivery mechanism which is arranged to automatically deliver a dose from the syringe, and optionally (particularly in the case of an autoinjector) to first displace the syringe, which may be held in a syringe carrier, within the housing to cause needle penetration. The delivery mechanism is typically released from an energised (or primed) position and may, for example, include one or more drive springs. The delivery mechanism may act upon a plunger which includes or acts against a piston (also referred to as a "bung") which is slidably provided within the syringe. In the case of an autoinjector the initial stiction between the piston and syringe may resist forward movement of the piston relative to the syringe such that initially the delivery mechanism moves the syringe (and syringe carrier) into the needle insertion position (whereupon further movement of the syringe is blocked and the delivery mechanism will continue to move forward thus moving the piston).

A trigger, for example in the form of a button on the end of the device, is generally provided to allow the user to activate the delivery sequence. Further, it is known to provide a moveable shroud assembly for safety reasons (for example to prevent accidental needle stick injuries) at the forward end of an injection device. The shroud assembly is generally configured to automatically move between a retracted position and extended position in which it shrouds (i.e. substantially surrounds) the needle after firing of the device. In the extended position the shroud is generally locked against retraction (i.e. movement back towards the retracted position).An autoinjector including a shroud assembly is, for example, disclosed in the applicant's earlier International Patent Application WO2012/085580A1. This application discloses an arrangement in which the shroud and syringe carrier are provided with cooperating features for controlling the extension of the shroud relative to the syringe carrier. Advantageously the cooperating features are formed integrally with the shroud and syringe carrier as the injection device is normally formed of injection moulded plastics material, and for ease and cost of manufacture and assembly, it is beneficial to have a low component count.

SUMMARY OF THE INVENTION

According to a first aspect of the invention there is provided an autoinjector device comprising: a body portion; a syringe carrier, for supporting a syringe with a needle at its forward end, the syringe carrier being moveably mounted within the housing such that forward movement relative to the housing may extend the needle from a forward end of the body, and the syringe carrier comprising a latch element arranged to cooperate with a corresponding retention feature of the body portion to releasably hold the syringe carrier in a rearward position within the body portion; a delivery mechanism arranged to forwardly displace the syringe carrier relative to the housing and to deliver a dose of medicament from the syringe; and a shroud assembly at a forward end of the device; and characterised in that the shroud further comprises a locking arrangement which blocks releasing movement of the latch element from the retention feature when the shroud is in a first, forward position and is unlocked when the shroud is in a second, rearward position.

The applicant has found that the provision of a locking arrangement between the shroud and the latch which must be unlocked by movement of the shroud may help prevent accidental or premature release of the shroud and/or the syringe carrier in the pre-use condition. For example, the locking arrangement may help prevent release in the event that the device is subject to an impact (such as being dropped) prior to use or during removal of the cap from the injection device. It will be appreciated that in normal use the shroud is only intended to move to its extended position after the injection has been complete and the device is removed from the injection site.

The retention feature of the body portion may be formed on an inner surface of the body portion. For example, the retention feature may extend inwardly (for example radially inwardly) from the body portion. The retention feature may, for example, comprise a surface, tab or ridge.

The rearward position of the syringe carrier may be a pre-use position. The delivery mechanism may be arranged to forwardly displace the syringe carrier relative to the housing by overcoming the hold of the latch element and retention feature.

The shroud assembly may generally be moveable between a retracted position and extended position (in which it shrouds the needle) relative to the body portion. The shroud may be configured to automatically move from the retracted position to the extended position after firing of the device (for example, in response to the injection device being removed from the injection site after firing). The shroud may be arranged to lock in the extended position.

The locking arrangement may be arranged to move out of blocking alignment with the latch element when the shroud is moved to the second, rearward position.

The shroud may be configured to move between the first, forward position and second, rearward position in response to the forward end of the autoinjector being pressed against an injection site (for example in preparation for use). For example, the forward end of the shroud may be pressed against the injection site in use causing the shroud to move rearwardly relative to the body portion. Both the first, forward position and second, rearward position of the shroud may be positions in which the shroud is retracted relative to the body housing (i.e. they are not the shrouding position).

The shroud may be biased towards the first, forward position. For example, the shroud may be forwardly biased by a shroud deployment spring (or springs). The shroud may be biased forwardly relative to the syringe carrier.

The shroud may be disposed between the body portion and the syringe carrier. The shroud may at least partially surround the syringe carrier. The locking arrangement may block inward movement (for example inward resilient deflection) of the latch element.

The latch element may be provided with a notched profile. The locking arrangement of the shroud may be positioned within the notch when blocking releasing movement of the latch element from the retention feature.

The latch element may comprise an outwardly projecting arm. The arm may be biased outwardly and may, for example, resiliently deflect inwardly to release the syringe carrier. The arm may project generally radially outwardly. The notch may be formed in a side portion of the arm.

The shroud may comprising a stop surface that cooperates with a stop surface on the latch element on said syringe carrier to limit the extent of forward movement of said shroud relative to said syringe carrier. For example, the shroud may comprise a longitudinal slot in which the latch element is received. The slot may delimit the longitudinal movement of the shroud relative to syringe carrier. The forward and rearward ends of the slot may form stop surfaces to limit longitudinal movement of the shroud relative to syringe carrier.

The locking arrangement may be formed by a rearward portion of the slot. The locking arrangement may comprise a portion of the slot having an opening of reduced width. For example, the surface adjacent to the reduced width portion of the slot may align with the notch of the latch element to block releasing movement of the latch element from the retention surface when the shroud is in the first, forward position.

The syringe carrier comprises a plurality of latch elements and the shroud may comprise a corresponding plurality of locking arrangements. For example the syringe carrier may comprise a pair of radially opposed latch elements and the shroud may comprise a corresponding pair of locking arrangements.

The autoinjector may further comprise a removable cap at the front end thereof. The cap may have a rearwardly extending portion which, when the cap is in place on the body portion, prevents inward movement of the latch element on said syringe carrier, but withdraws on removal of said latch to allow inward movement.

The shroud may include a further latch element. The shroud latch element may be disposed adjacent or forwardly of the retention feature on the body portion. The shroud latch element may be arranged to limit rearward movement of the shroud beyond the second, rearward position in pre-use configuration. Forward movement of the shroud in the pre-use configuration may be limited by the interaction between the shroud and the syringe carrier (for example by the latch element and slot).

The syringe carrier may include at least one further latch element disposed rearwardly of said (at least one) first-mentioned latch element. The further latch element may be arranged to cooperate with the latch element on the body portion to limit or prevent retraction of said shroud (after the shroud has extended at the end of an injection).

According to a further aspect of the present invention, there is provided an injection device comprising: a housing; a syringe having a barrel and a piston disposed within the barrel and moveable between a rearward position and a forward position to urge medicament from a forward end of the syringe; the syringe being mounted within the housing; a delivery mechanism arranged to act upon a plunger which includes or acts against the piston; and wherein the housing comprises a window or viewing aperture extending along a longitudinal section of the syringe barrel through which the contents of the syringe or capsule may be inspected in use, the window or aperture being divided into forward and rearward portions, the forward portion being substantially aligned with the position of the plunger when the delivery of the medicament is complete.

Thus, the viewing window may be arranged such that it is immediately apparent to then end user when the piston of the syringe reaches or approaches the final delivery position (as it moves into the forward window portion).

The division between the forward and rearward portions could simply be provided by a marking or indication formed on the window. However, the window or viewing aperture may be divided by a transverse member (i.e. extending transverse to the longitudinal syringe barrel).

The window or viewing aperture may comprise a plurality of aligned windows or apertures formed in the components of the injection device which surround the syringe barrel, in use. For example windows or apertures may be formed in the housing and the syringe carrier. At least one of the windows or apertures may be a transparent window (for example the outer housing).

The injection device may further comprise a syringe carrier. The syringe carrier including may include the window or aperture being divided into forward and rearward portions. For example the syringe carrier may comprise at least two viewing apertures separated by a transverse member. Advantageously, the syringe carrier is fixed relative to the syringe (but both may move relative to the housing) and, therefore, may provide an accurate positioning of the forward and rearward portions.

The housing may include a window overlying the apertures or windows of the viewing aperture. For example, a portion of the housing may be made from a generally transparent material.

Whilst the invention has been described above, it extends to any inventive combination or sub-combination of novel features set out above, or in the following description or claims.

BRIEF DESCRIPTION OF THE DRAWINGS

The invention may be performed in various ways and an embodiment thereof, with various modifications, will now be described by way of example only, reference being made to the accompanying drawings in which.

DETAILED DESCRIPTION OF EMBODIMENTS

Front as used herein will be understood to refer to the end of the injector assembly (or components thereof) which, in use, are closest to the delivery needle delivery end of the injector (i.e. the end which is pointed at the skin). Rear as used herein will be understood to refer to the end of the pen injector assembly (or components thereof) which, in use, are furthest from the needle delivery end of the injector (i.e. the end which is pointed away from the skin). Forward and rearward will, likewise, be understood to refer to the directions orientated towards the front and rear of the injector assembly.

Axial, radial and circumferential are used herein to conveniently refer to the general directions relative to the longitudinal direction of the injection device (or components thereof). The skilled person will, however, appreciated that these terms are intended to be broadly interpreted (and for example, the injection device may have a non-circular and/or irregular form). Typically, regardless of the chosen injector device external profile the cartridge or syringe will have a conventional generally cylindrical form and, as such, the longitudinal axis of the injection device will substantially coincide with (or be parallel to) the axial direction of the syringe.

Figure 1:
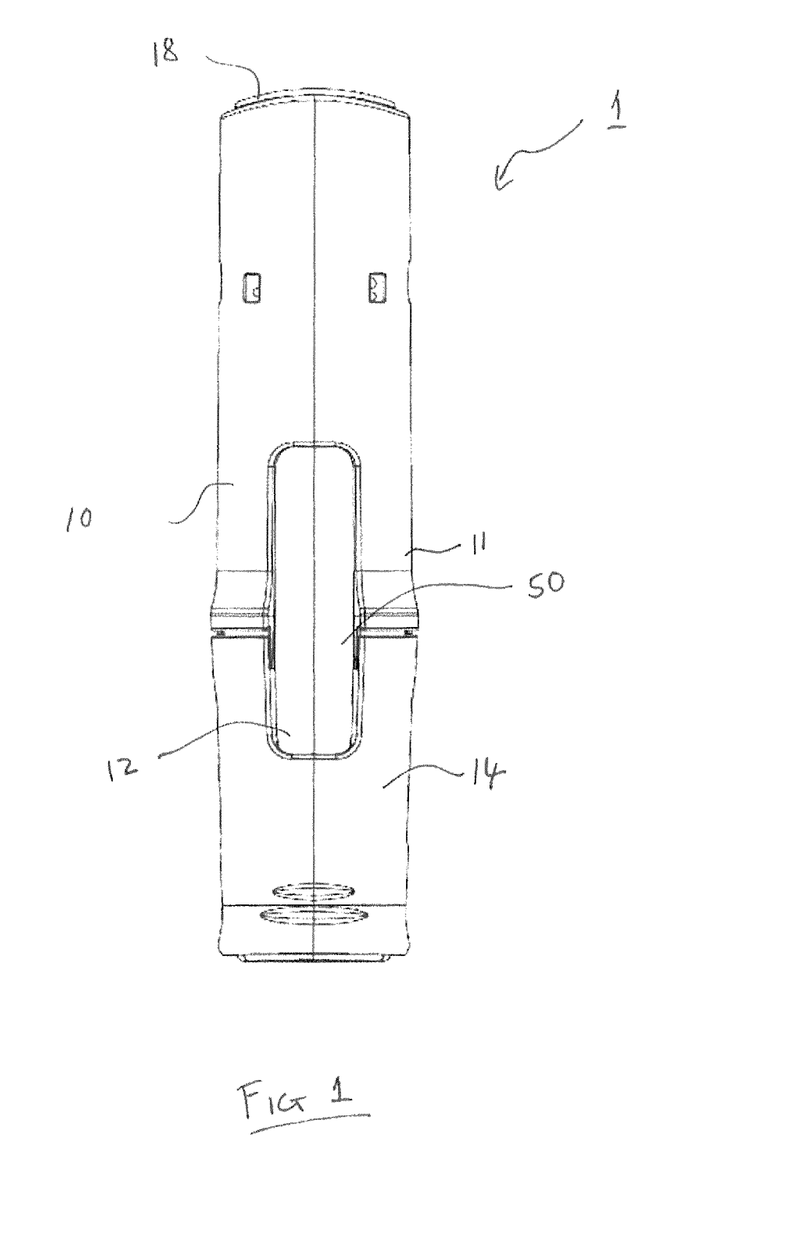
FIG. 1 is an injection device according to an embodiment of the invention.

An autoinjector 1 in accordance with an embodiment is generally shown in FIG. 1. The autoinjector comprises a housing 10, having a removable cap 14 at a forward end and a trigger button 18 at a rearward end (although the skilled person will appreciate that in some injector devices the activation trigger may not include a separate button but may instead be activated in response to the device being pressed against the skin).

Figure 2:
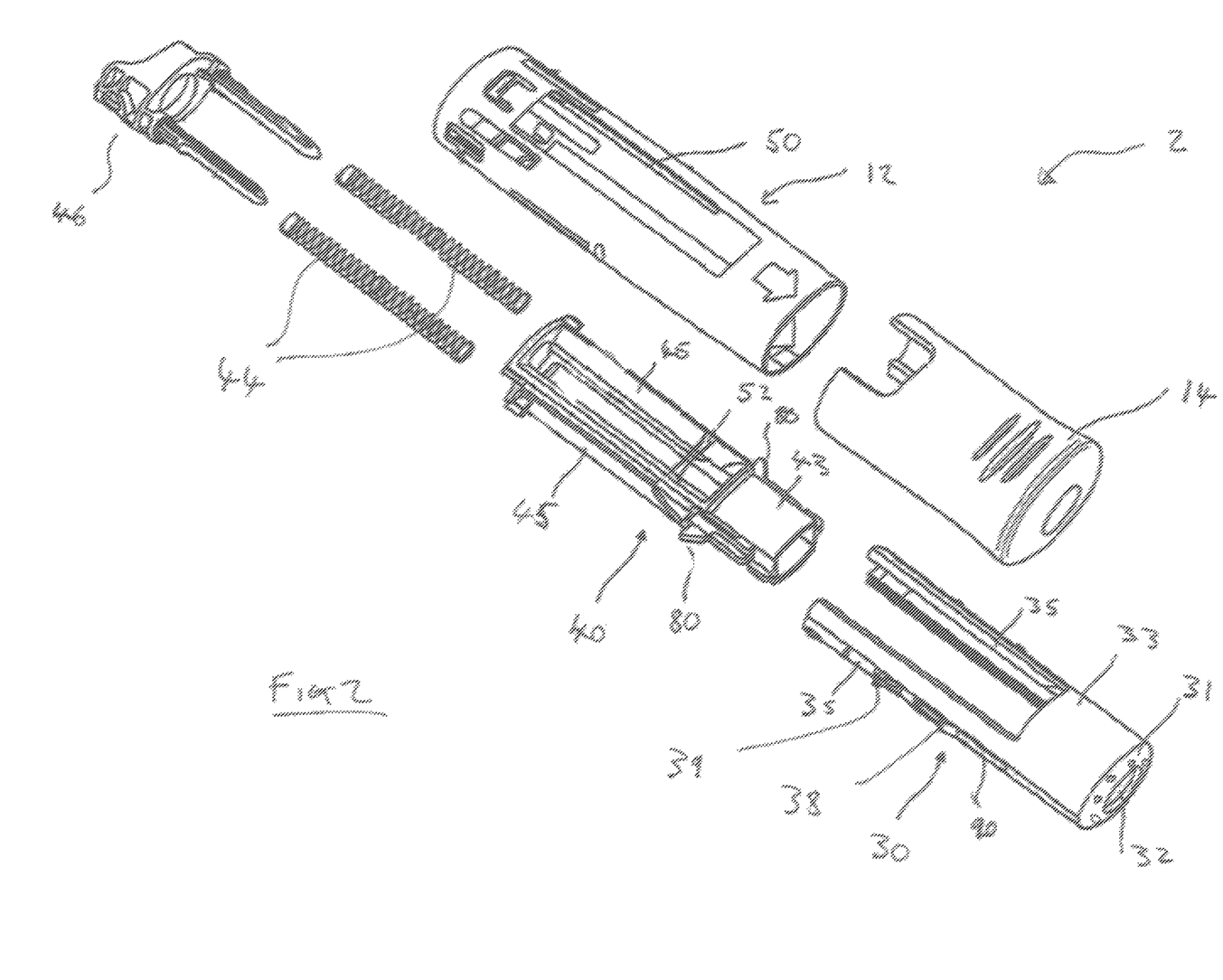
FIG. 2 is an exploded view of a front assembly of an injection device in accordance with an embodiment.

In the illustrated embodiment the injector is generally of the type disclosed in WO2012/085580A1 and includes a forward assembly as shown in FIG. 2 in which twin shroud springs 44 are provided to forwardly bias the shroud 30 relative to a syringe carrier 40. The shroud springs 44 are spaced to either side of longitudinal axis of the device to allow the entire length of the dose volume to be visible through a viewing window 50 formed in the housing 10 without being obscured by any springs.

The illustrated embodiment includes a housing 10 which comprises a rearward portion 11 and a forward portion 12 which are relatively slidable as part of the activation sequence (to provide an interlock arrangement). Thus, the injector may include a delivery mechanism which is substantially of the type disclosed in the applicant's co-pending patent application GB1417522.8. It will, however, be appreciated that embodiments of the invention may be utilised with various known types of injection device. In particular, the invention is not limited to any particular delivery mechanism (and as such the delivery mechanism is not described herein) but typically, the delivery mechanism may include a plunger which is held in an initial latched position against the force of a drive spring, the plunger being released by the trigger arrangement to allow the plunger to be driven forwardly by the drive spring.

As seen in the exploded view of the front assembly 2 (of FIG. 2), the front assembly 2 comprises an outer body housing 12 of generally clear plastic material. The housing defines two opposed viewing windows 50 which are described in further detail below.

Slideably mounted within the forward housing 12 is a needle shroud 30 having a textured front face 31 (which is provided with a series of forwardly extending projections to provide a nerve confusion effect) and a central aperture 32 therein to provide through which the needle of the syringe may project during the injection. The shroud 30 includes two rearwardly extending arms 35 of arcuate cross-section, extending back from a forward tubular section 33.

Slideably coupled to the needle shroud 30 is a syringe carrier 40 having a forward tubular portion 43 capable of sliding telescopically inside the tubular portion 33 of the needle shroud 30. Extending rearwardly from the tubular portion 43 of the syringe carrier 40 are two arms 45 having opposed inner concave surfaces for slideably receiving the barrel of a syringe. The arms 45 have outer concave surfaces defining, with convex inner arcuate surfaces on the arms 35 of the needle shroud 24, cylindrical containment spaces for a pair of shroud springs 44. A spring guide 46 is attached to the rearward end of the syringe carrier and includes two forwardly extending fingers that pass down the centre of a respective spring 44.

As will be explained in further detail below, the syringe carrier 40 is provided with a pair of opposing radially outwardly extending latch tabs 80. The latch tabs 80 are arranged to cooperate with a corresponding feature 20 formed on the inner surface of the forward body housing 12 to hold the syringe 40 in a rearward, pre-use, position. The tabs 80 are integrally formed with the syringe carrier 40 but are resiliently connected via sprung arms (such that they may be deflected to disengage the feature 20). When the syringe carrier 40 is assembled telescopically into the needle shroud 30 (to assembly the injector device) the tabs 80 are received within, and project through, slots 90 in the shroud 24. The slots 90 extend longitudinally along the arms 35 of the shroud 30. The interaction between the tabs 80 and the slots 90 limit the relative longitudinal movement of the shroud 30 relative to the syringe carrier 40.

It may be noted that the features of the needle shroud 30 and syringe carrier 40 as described above are substantially similar to that of WO2012/085580A1. However, the arrangement according to embodiments of the invention has been further modified to provide an arrangement in which the shroud 30 and syringe carrier 40 are provided with a locking arrangement to prevent premature unlatching. Advantageously, the arrangement of embodiments of the invention may provide such a locking feature without requiring any additional components.

Figure 3A:
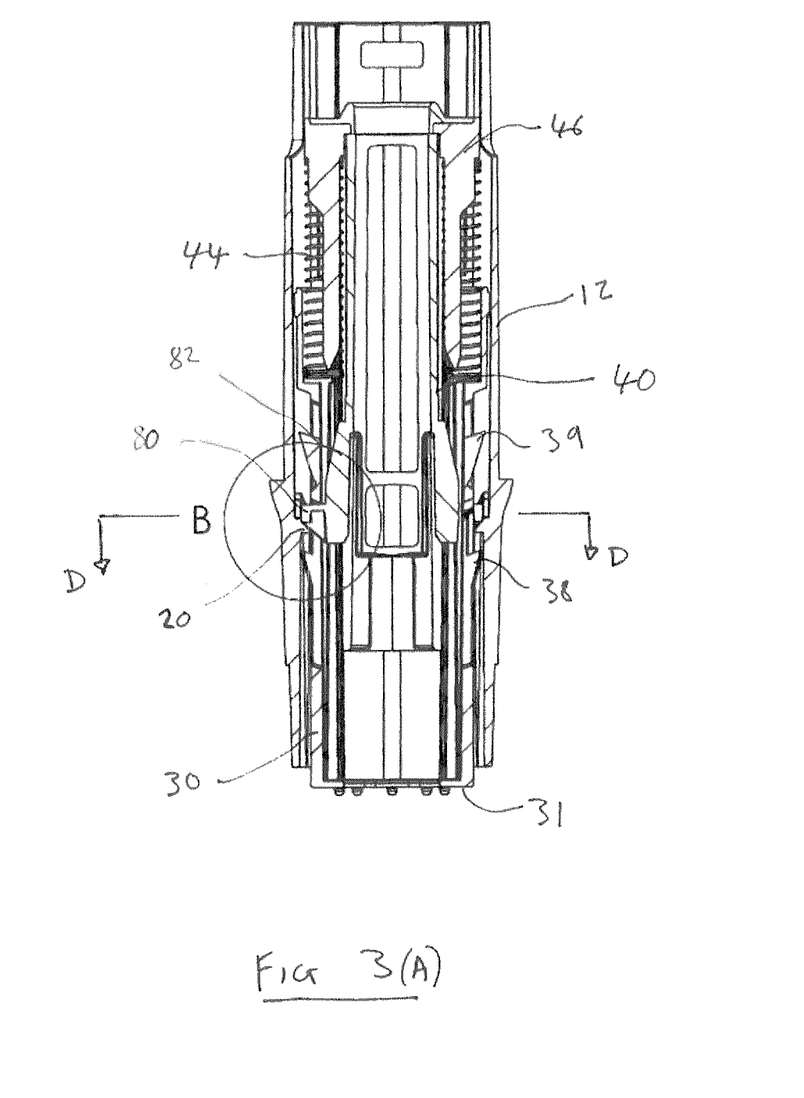
FIG. 3(A) is a transverse cross section through the major axis of the injector device front assembly in accordance with an embodiment in a pre-use configuration.
Figure 3B:
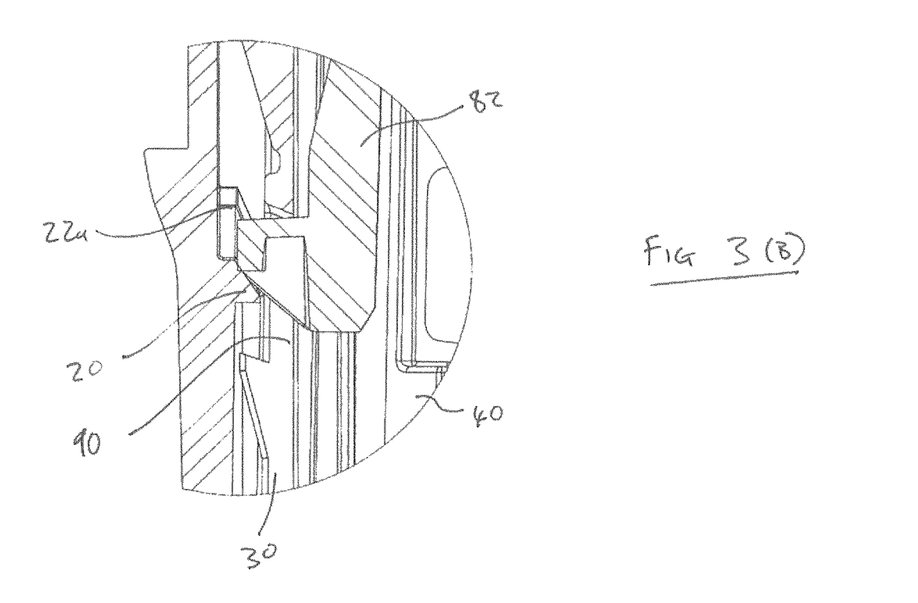
FIG. 3(B) is a detail of the cross-section of FIG. 3(A)
Figure 3C:
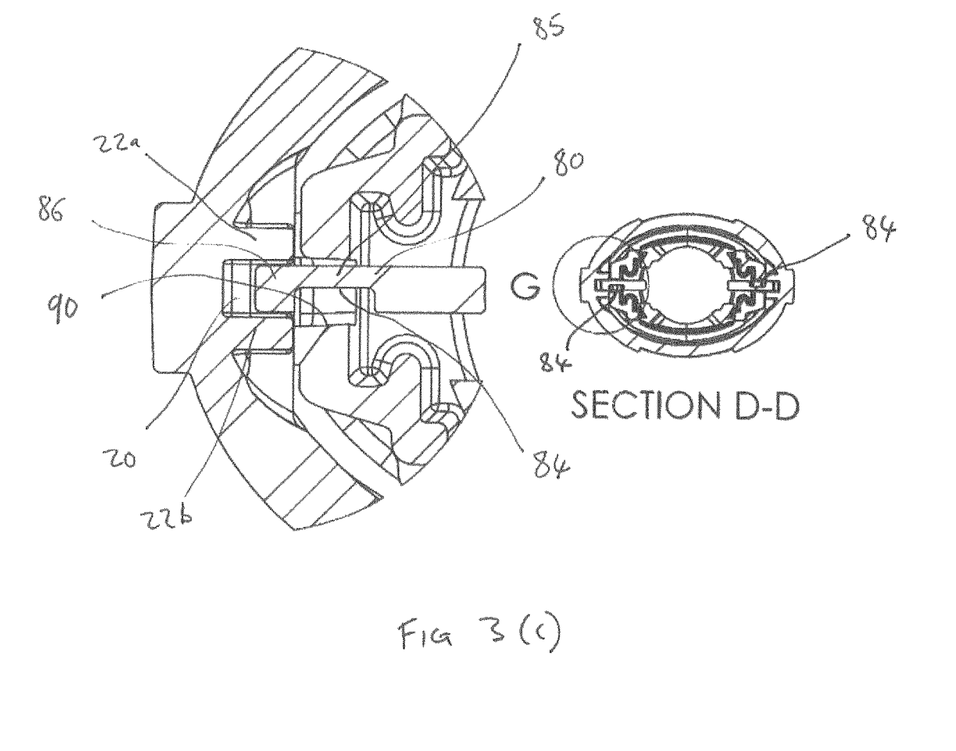
FIG. 3(C) is a view and detail through section D-D of FIG. 3(A)

As shown in FIG. 3 (in which it may be noted that the syringe 3 has been omitted from FIGS. 3(A) to 3(C) for clarity), in the pre-use configuration the syringe carrier 40 is in its initial (rearward position) relative to the forward housing 12. The drive mechanism (not shown) provided in the rearward body portion would be arranged to act upon the syringe and syringe carrier 40 to provide a forward drive force but would be initially held or latched against this force until release by the trigger.

In the initial position of FIG. 3 the syringe carrier 40 is latched relative to the forward body housing 12 by the latch tab 80 abutting the corresponding radially inwardly directed latch features 20 formed on the inner surface of the body. As best seen in FIGS. 3(A) and 3(D) it will noted that the inward projection 20 slopes inwardly in a forward direction but has a stepped profile at its forward face. A pair of inward alignment surfaces 22a and 22b are provided immediately rearward of the projection 20 (as best seen in FIG. 3(C)) and serve to align the latch tab 80 and projection 20.

Figure 3D:
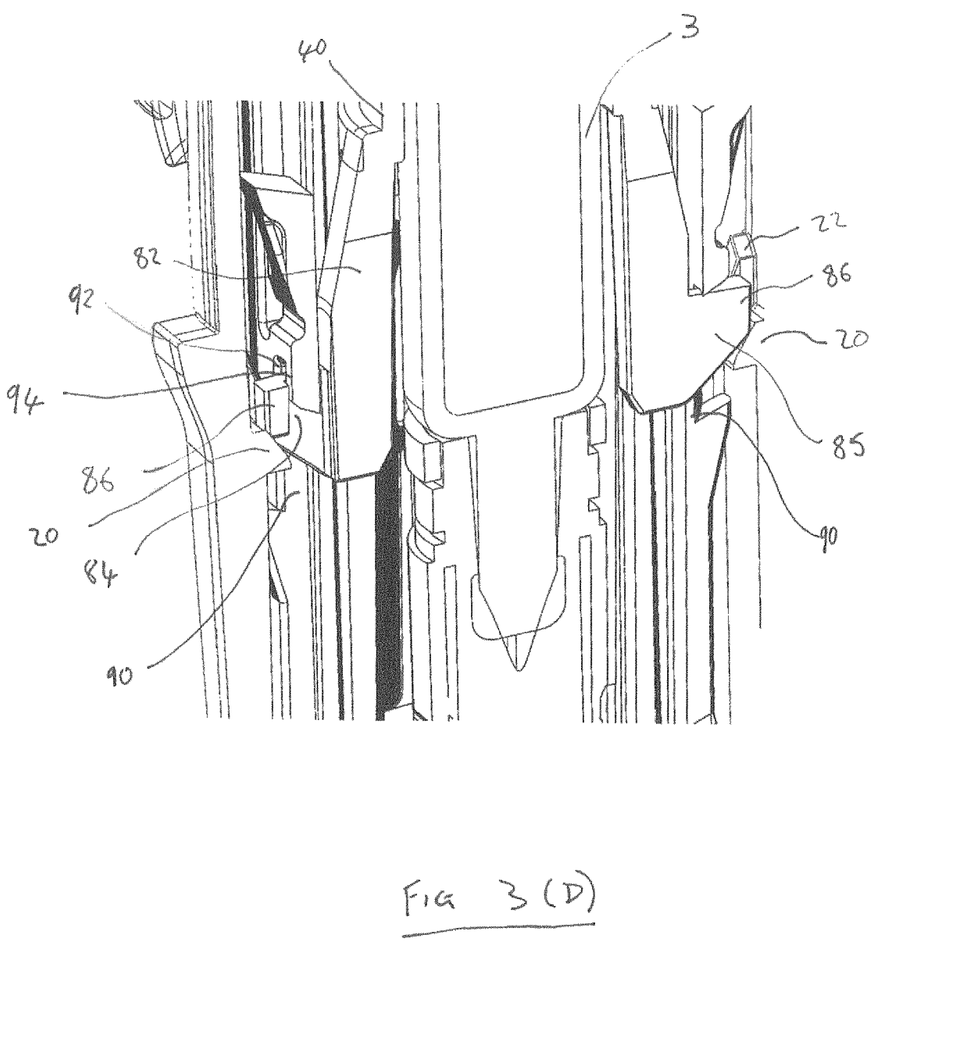
FIG. 3(D) is a three-dimensional cross section of the front assembly (including a syringe)

The latch tab 80 is formed on a sprung finger 82 which extends from the body of the syringe carrier 40. In use the arm 82 enables the latch tab 80 to resiliently deflect inwardly toward the syringe carrier 40 (and biases the latch tab 80 toward its extended radially outward position). As best seen in FIGS. 3(C) and 3(D), the latch tab 80 comprises a head 86 at its radially outermost end and a notched section 84 which is, in the initial position, radially aligned with the slot 90 of the needle shroud 30. Thus, the latch tab 80 has a reduced thickness neck 85 radially inwardly of the head 86. It may be noted that in the illustrated example, the neck 85 is formed by a notch 84 on only a single side of the latch tab 80. Further, as seen in FIG. 3(E), the latch element 80 on opposing sides of the device is provided with notches 84 which are on opposite sides of the latch element 80.

When the injection device is in the pre-used configuration, the syringe carrier 40 may be fixed relative to the housing 12 (with forward movement of the syringe carrier 40 being resisted by latch 80/projection 20 and rearward movement being prevented by the position of the syringe and delivery mechanism). The shroud 30 is forwardly biased relative to the syringe carrier 40 by the shroud springs 44 (which are attached to the syringe carrier 40 by the spring carrier 46). The forward movement of the syringe carrier 30 is limited by the latch tabs 80 abutting against a rearward stop surface formed at the end of the slot 90. In this pre-used configuration, the front end 31 of the needle shroud 30 projects forwardly by a small distance beyond the forward end of the body housing 12.

Figure 3E:
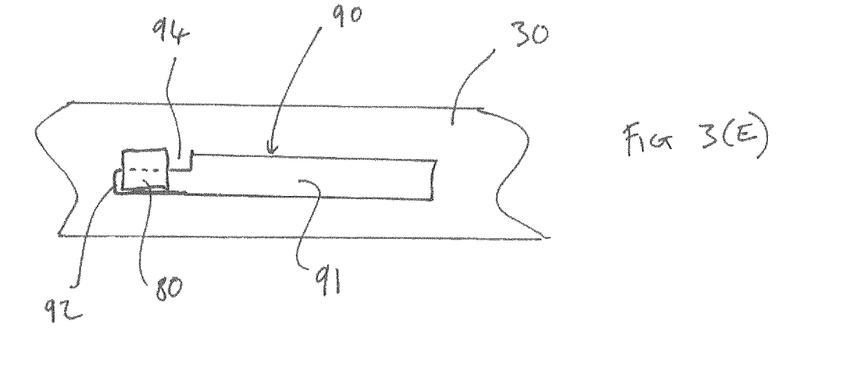
FIG. 3(E) is a schematic representation of the slot formed in the needle shroud in accordance with an embodiment.

As shown schematically in FIG. 3(E), the rearward end of the slot 90 is provided with a locking surface 94 which is formed by the rearward portion of the slot 92 having a reduced width in comparison to the main portion 91 of the slot 90. In particular, it will be noted that in the pre-use position of FIG. 3(A) to 3(D), the neck 85 of the latch tab 80 is positioned within the reduced width section 92 such that the head 86 overhangs the locking surface 94 and the reduced thickness neck 85 is positioned within the reduced width end 92 of the slot 90. Thus, in the initial configuration it is not possible for the latch tabs 80 to be displaced radially inwardly out of the head 86 as inward radial movement is blocked by the locking surface 94 of the slot 90 underlying the head 86.

Figure 4A:
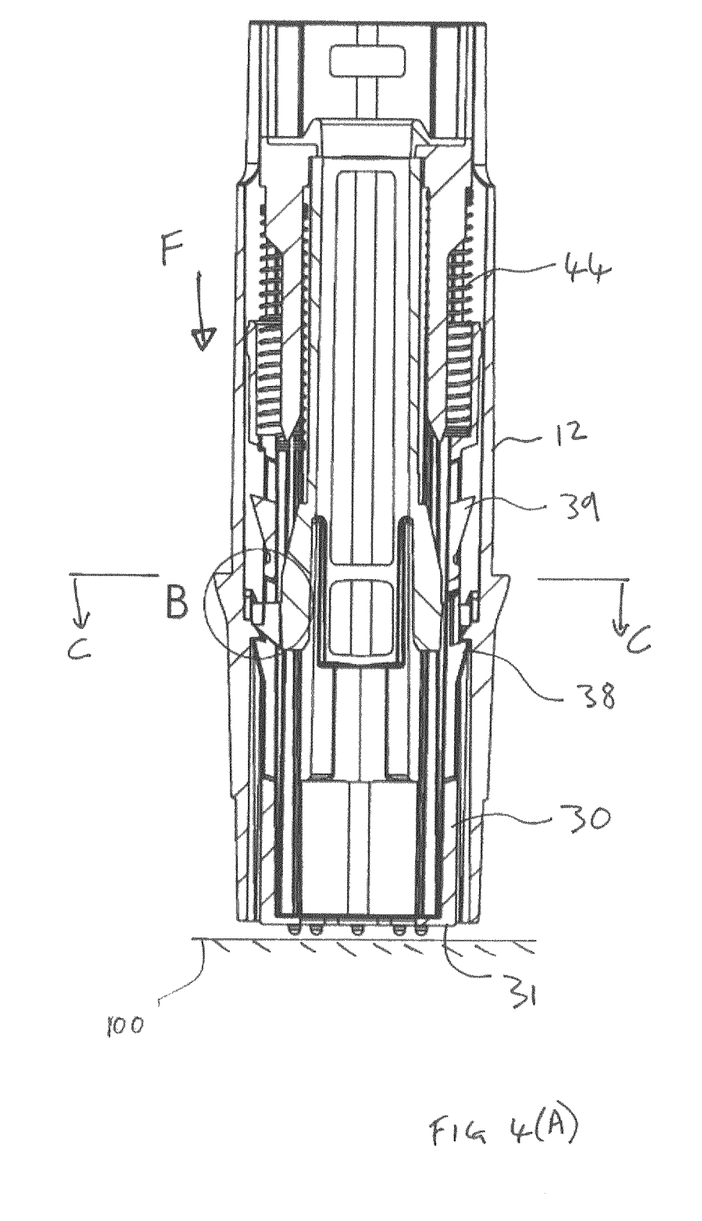
FIG. 4(A) is a transverse cross-section of the front assembly of FIG. 3 in a ready-to-use configuration.
Figure 4B:
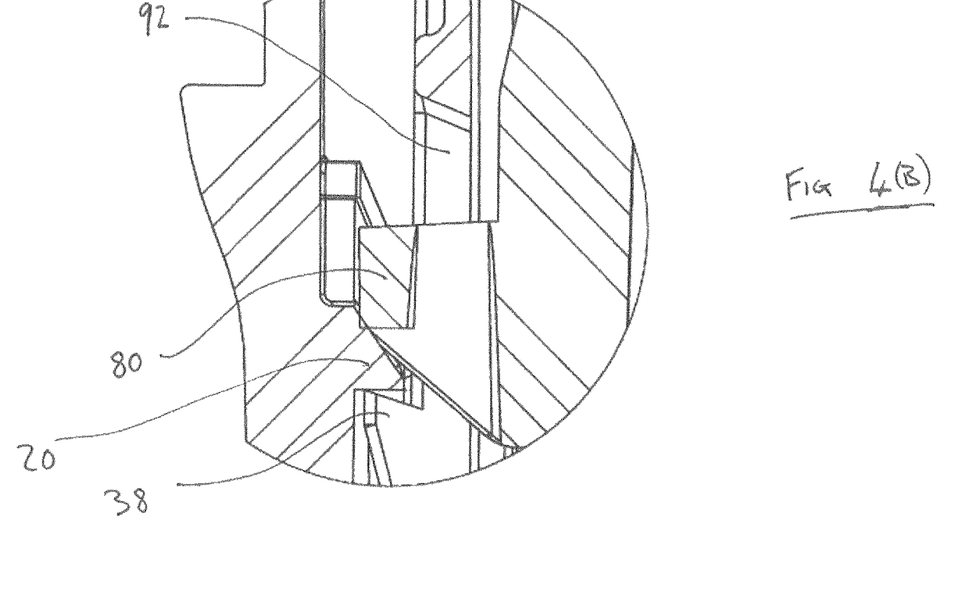
FIG. 4(B) is a detail of the cross-section of FIG. 4(A)
Figure 4C:
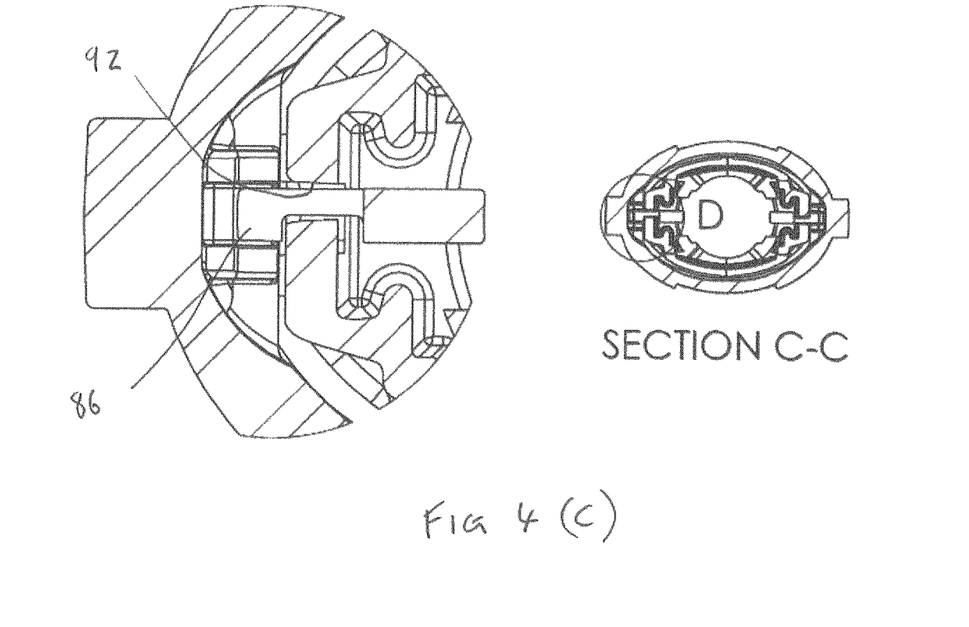
FIG. 4(C) is a view and detail through section C-C of FIG. 3(A)
Figure 4D:
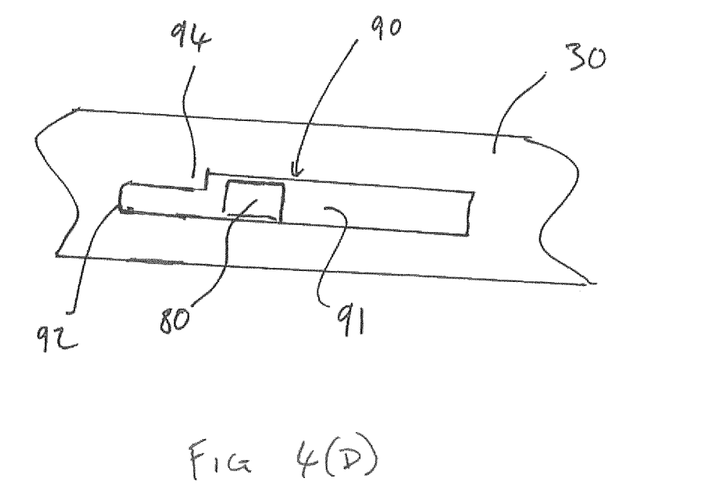
FIG. 4(D) provides a detail of the device of FIG. 4(A)

In order to activate the injection device, the user must first press the forward end of the injector against an injection site 100 such that the force F on the outer body 10 moves the needle shroud 30 rearwardly relative to both the body portion 10 and the syringe carrier 40. This initial movement compresses the shroud springs 44. As shown in FIGS. 4(B) and 4(C) and schematically in FIG. 4(D), the rearward movement of the shroud 30 moves the latch tab 80 away from the seat at the rear end 92 of the slot 90. The longitudinal length of the locking portion 94 is selected such that the head 86 of the locking tab 80 moves out of the locking surface 94 and into the full width section 91 as a result of the rearward movement of the shroud 30. Thus, in the configuration of FIG. 4 in which the injector is pressed against an injection site, the injector may be considered to be ready to fire since the delivery mechanism may now urge the syringe carrier 40 forwardly within the housing to cause the latch tabs 80 to cam inwardly across the sloped surface of the inward projection 20 without any obstruction from the slot 90 of the shroud 30. Due to the opposing side arrangements of the notches 84 of the latching members 80, the syringe carrier 40 may conveniently rotate slightly relative to the needle shroud 30 as the latch tab 80 moves along the slot 90.

The rearward movement of the shroud 30 relative to the forward housing 12 is limited by a latch element 38 positioned forwardly of the rear end 92 of the slot 90 which prevents movement of the shroud 30 by engaging the forward stepped surface of the projection 20. It will have been noted that the latch element 38 has a sloped forward surface to allow it to be slid beyond the projection 20 during assembly of the injection device.

With the injection device in the ready configuration of the FIG. 4, the user triggers the device (for example by pressing a trigger button or by further urging the device against the injection site 100). This causes a drive mechanism to be released which may for example drive a plunger 15 forwardly using a drive spring 16. Initially, the drive mechanism will (due to the stiction of the piston of the syringe 3 and the incompressibility of medicament) move the syringe 3 and syringe carrier 40 forwardly overcoming the latch hold of the latch tabs 80 and projections 20. Thus, the latch tabs 80 will deflect radially inwardly past the projection 20 and spring back radially outwardly one they reach a forward position. The latch elements 80 will then continue to slide forwardly within the slot 90 of the shroud 30 until the syringe holder 40 has reached its fully forward position. In this position the latch tab 80 will reach the forward stop surface of the slot 90 and a forward surface of the cylindrical portion 43 of the syringe carrier 40 may also move into abutment with the rear surface of the forward face 31 of the needle shroud 30. The skilled person will appreciate that in this position the needle 4 of the syringe 3 will be extending beyond the forward end of the needle shroud 30 through the aperture 32 so as to pierce the skin. The delivery mechanism will continue to drive the plunger forwardly so as to dispel a dose of medicament from the syringe 3.

Figure 5A:
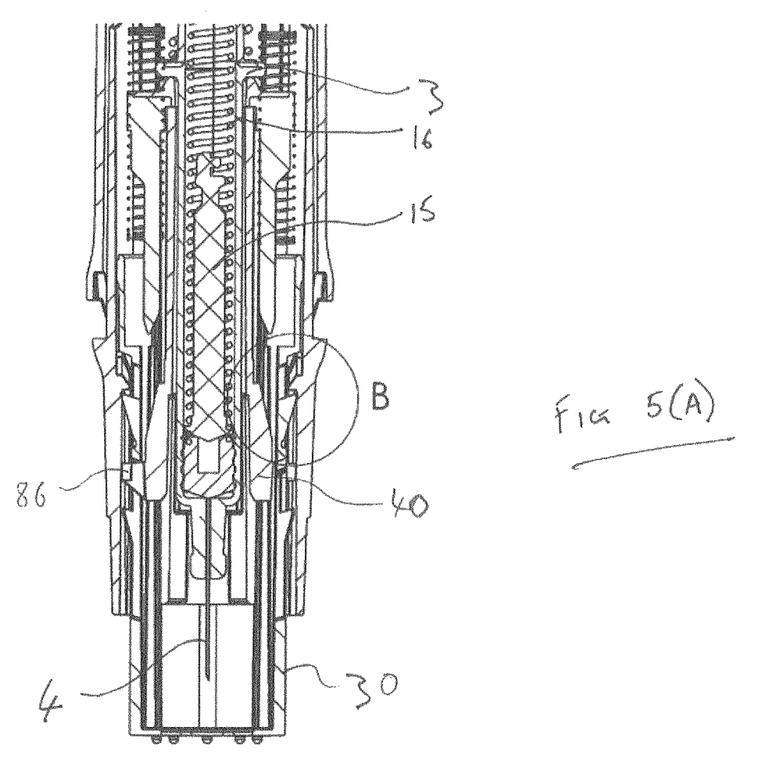
FIG. 5(A) is a transverse cross-section through of the front assembly of FIG. 3 in a post-use configuration.
Figure 5B:
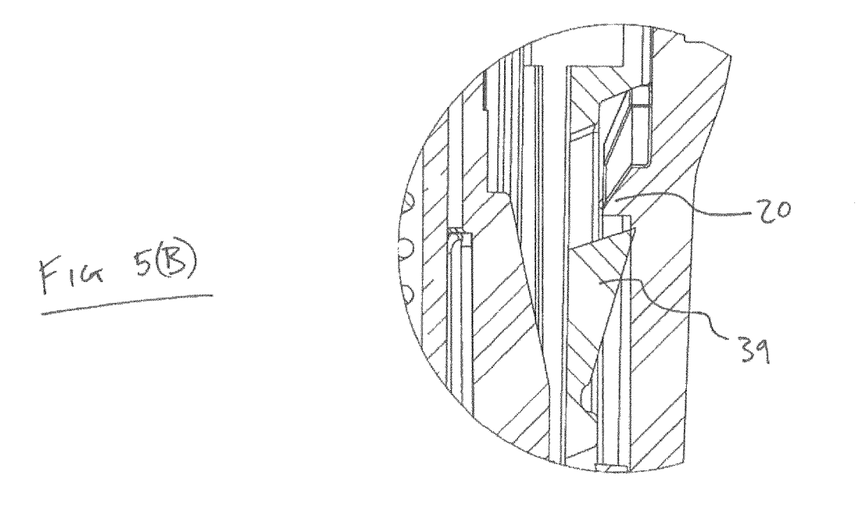
FIG. 5(B) is a detail of the cross-section of FIG. 5(A)

During delivery the needle shroud 30 has remained in the position shown in FIG. 4 and, as such, the movement of the syringe carrier 40 will cause the shroud springs 44 to be compressed. As shown in FIG. 5 (in which the syringe 3 and needle 4 are shown for completeness), upon removal of the device from the injection site the shroud springs 44 will move the needle shroud 30 forward relative to the forward housing 12 and syringe carrier 40. The forward movement of the needle shroud 30 is limited by the interaction between the latch tab 80 and slot 90 with the forward most position of the needle shroud 30 being when the latch tab 80 reaches the rear portion 92 of the slot 90. Additional barbed latched elements 39 provided rearwardly of each slot 90 snap past the projection 20 of the forward body housing 12 to lock the needle shroud in its extended position and ensure that the needle 4 is safely shrouded.

As mentioned above, injector devices in accordance with embodiments of the invention may include a viewing window 50 which enables the user to view the syringe and medicament therein. Generally the device may comprise a pair of identical viewing windows or closing sides of the syringe so as to allow the user a clear view (since the device may if necessary be held up to a light source). In accordance with embodiments of the invention, the viewing window 50 is divided by a transverse member 52 so as to define a forward window portion 54 and a rearward window portion 56.

FIG. 6 shows external views of the injected device during the sequence of operation so as to illustrate the function of the viewing window 50. In a pre-use condition shown in FIG. 6(A) the device is fitted with a cap 14 at its forward end and it will be seen that the cap 14 and rear housing 11 include aligned U shaped sections which together act to frame the viewing window 50. In this position, the user can clearly see the syringe within the window 56 and with substantially the full filled length of the syringe 3 being visible.

Figure 6A:
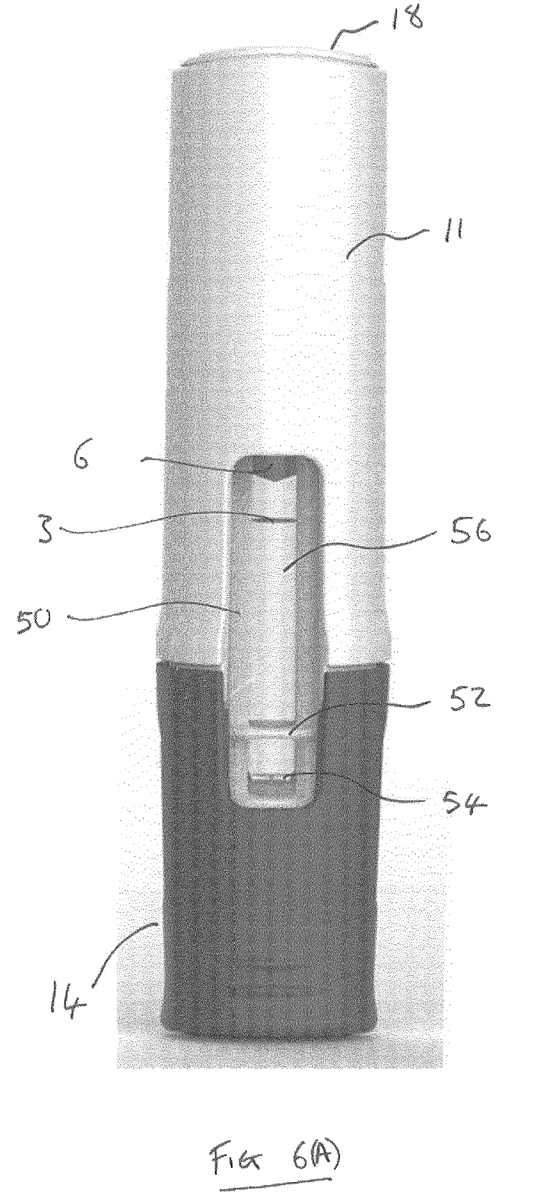
FIG. 6 are schematic external views of an injector device according to an embodiment illustrating the operating sequence.
Figure 6B:
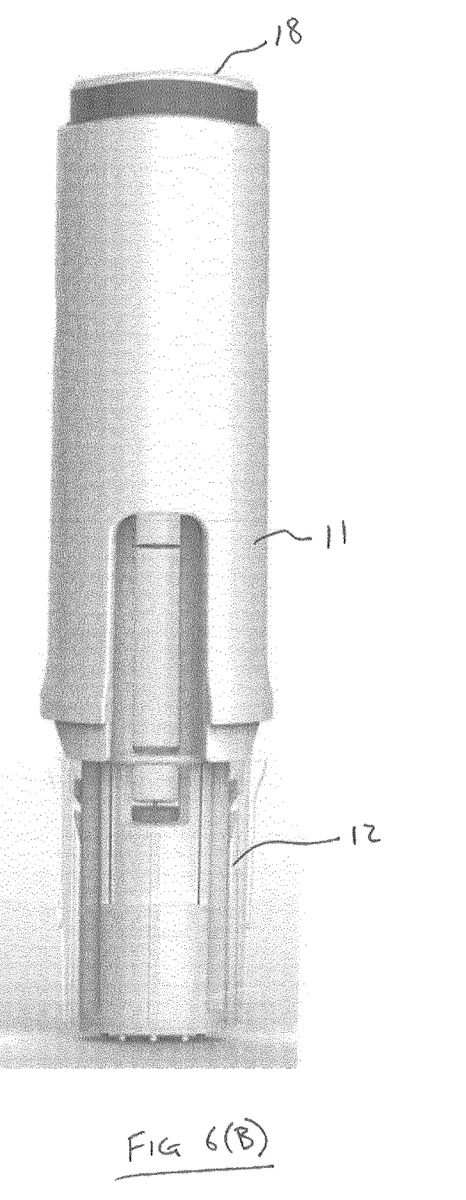

To use the device, the user removes the cap 14 from the forward end and presses the front body housing 12 against the injection site causing the rearward body housing 11 to slide forwardly as shown in FIG. 6b. It may be noted that in this position the trigger button 18 at the rear of the device has become visible due to the movement of the rearward body housing 11. It can also be noted in this figure that the forward body housing 12 is made up from a substantially transparent material which provides an advantage in ensuring that the syringe is fully enclosed. The forward body housing 12 extends rearwardly beyond the viewing window 50 and is connected within the rearward body housing 11.

Figure 6C:
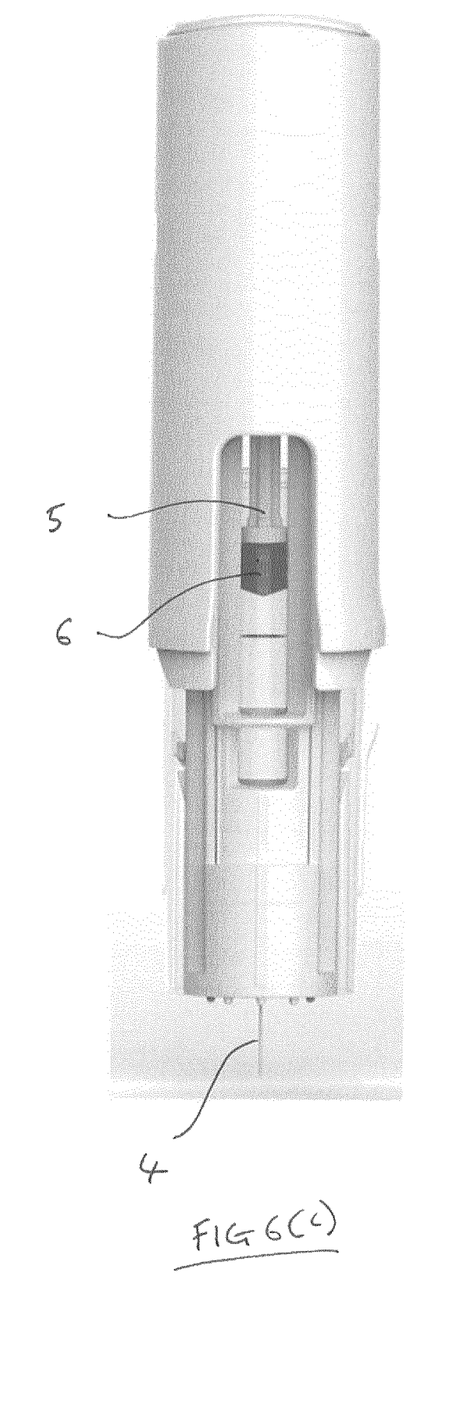

As shown in FIG. 6(C), after the trigger 18 has been forwardly depressed to release the delivery mechanism the delivery mechanism acts upon the plunger 5. Initially the plunger 5 drives the syringe and syringe carrier forwardly such that the needle 4 may extend beyond the forward end of the device to pierce the skin and subsequently to displace the piston 6 within the syringe 3. During this action the piston 6 becomes visible in the rearward portion 56 of the window 50 and its forward movement can be observed to see that the delivery is proceeding.

Figure 6D:
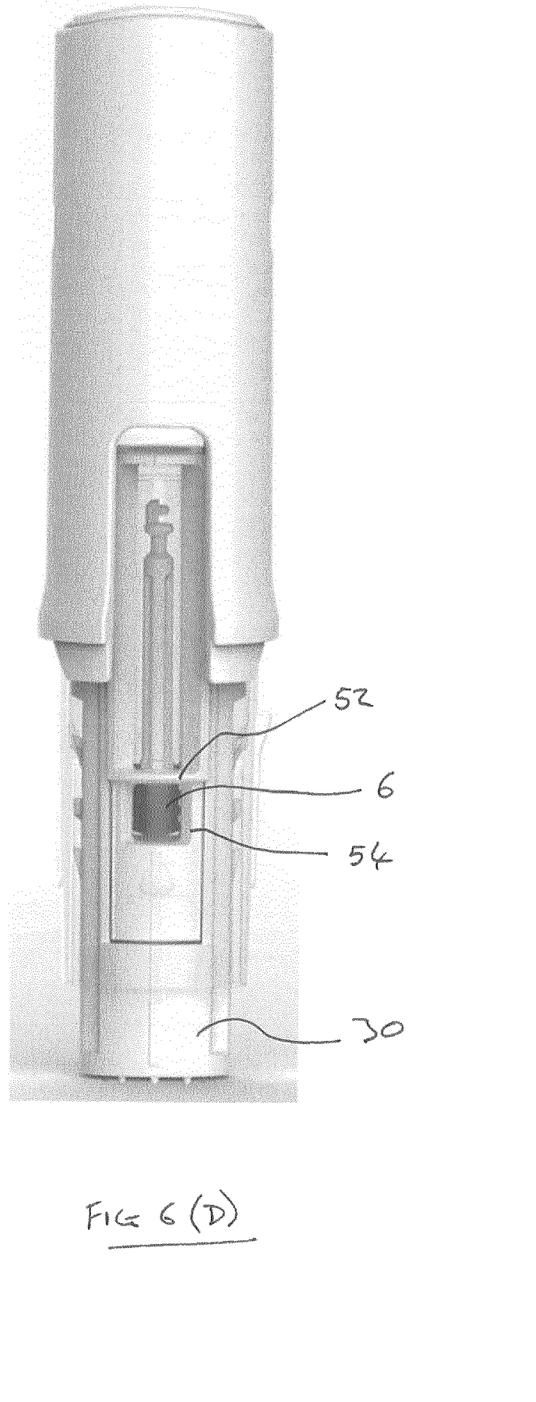
Figure 7:
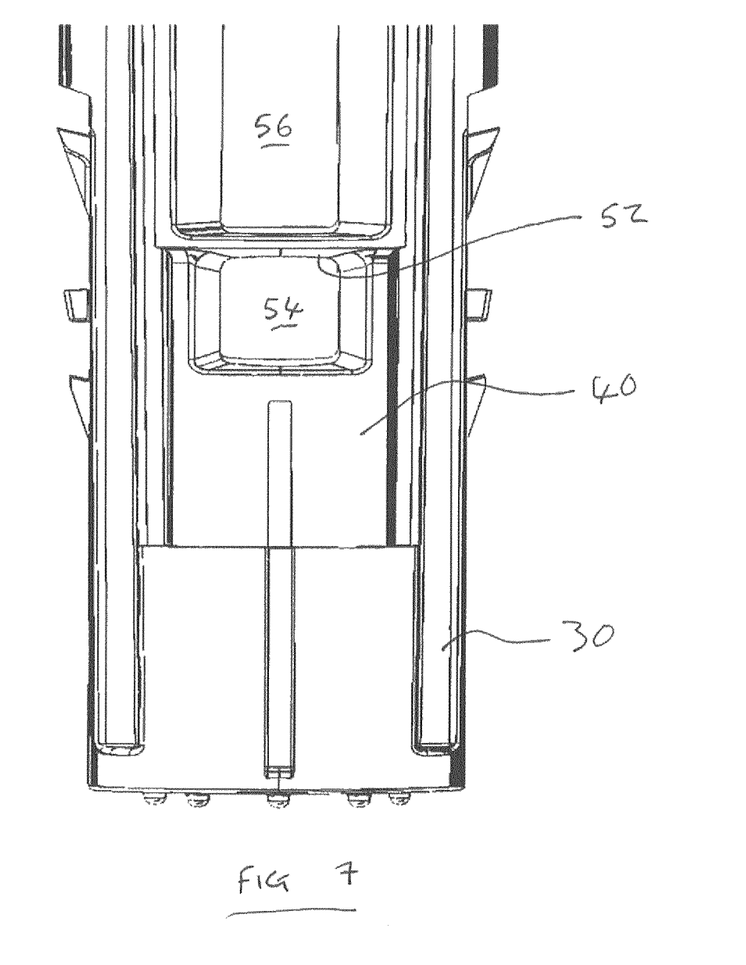
FIG. 7 is a detail of the syringe carrier and shroud according to an embodiment of the invention.

As the plunger 5 reaches its forward most position, the piston 6 moves into the portion of the syringe 3 which is aligned with the forward window portion 54. As such, the transverse section 52 dividing the forward and rearward viewing window portions 54, 56 provides the end user with an immediate and self explanatory indication that the injection is complete (or at least is approaching completion). In a final step of the use, the injector device is removed from the skin and the needle shroud 30 moves forward relative to the front body 12 and syringe carrier to shroud the needle 4 as shown in FIG. 6(D). Whilst the divider 52 between the forward 54 and rearward 56 window portions could be formed by a marking or indication provided on the covering window on the outer body 12, it is particularly convenient to form the window by a physical transverse frame 52 moulded as part of the syringe carrier 40. In particular, forming the separating frame 52 in the syringe carrier 40 avoids the need to account for the relative movement between the syringe 3 and housing 10 during operation (since the syringe carrier 40 is generally fixed relative to the syringe).

Although the invention has been described above with reference to a preferred embodiment, it will be appreciated that various changes or modifications may be made without departing from the scope of the invention as defined in the appended claims.

The invention claimed is:

1. An autoinjector device comprising:
a body portion;
a syringe carrier, for supporting a syringe with a needle at a forward end, the syringe carrier being moveably mounted within the body portion such that forward movement relative to the body portion extends the needle from a forward end of the body portion, and the syringe carrier comprising a latch element arranged to cooperate with a corresponding retention feature of the body portion to releasably hold the syringe carrier in a rearward position within the body portion;
a delivery mechanism arranged to forwardly displace the syringe carrier relative to the body portion and to deliver a dose of medicament from the syringe; and
a shroud at a forward end of the device, the shroud comprising a locking arrangement which blocks releasing movement of the latch element from the retention feature when the shroud is in a first, forward position and is unlocked when the shroud is in a second, rearward position, the shroud further comprising a stop surface that cooperates with a stop surface on the latch element of the syringe carrier to limit the extent of forward movement of the shroud relative to the syringe carrier.

2. An autoinjector as claimed in claim 1, wherein the shroud moves between the first, forward position and the second, rearward position in response to the forward end of the autoinjector being pressed against an injection site.

3. An autoinjector as claimed in claim 1, wherein the shroud is biased towards the first, forward position.

4. An autoinjector as claimed in claim 1, wherein the shroud is disposed between the body portion and the syringe carrier and wherein the locking arrangement blocks inward movement of the latch element.

5. An autoinjector as claimed in claim 4, wherein the latch element is provided with a notched and the locking arrangement of the shroud is positioned within the notch when blocking releasing movement of the latch element from the retention feature.

6. An autoinjector as claimed in claim 4, wherein the latch element comprises an outwardly projecting arm.

7. An autoinjector as claimed in claim 1, wherein the shroud comprises a longitudinal slot in which the latch element is received, the slot delimiting the longitudinal movement of the shroud relative to syringe carrier.

8. An autoinjector as claimed in claim 7, wherein the locking arrangement is formed by a rearward portion of the slot.

9. An autoinjector as claimed in claim 8, wherein the locking arrangement comprises a portion of the slot having an opening of reduced width.

10. An autoinjector as claimed in claim 1, wherein the syringe carrier comprises a pair of radially opposed latch elements and the shroud comprises a corresponding pair of locking arrangements.

11. An autoinjector as claimed in claim 1, wherein the autoinjector includes a removeable cap at the front end thereof, the removeable cap having a rearwardly extending portion which, when the removeable cap is in place on the body portion, prevents inward movement of the latch element on the syringe carrier, but withdraws on removal of the latch to allow inward movement.

12. An autoinjector as claimed in claim 1, wherein the shroud includes a latch element disposed adjacent or forwardly of the retention feature on the body portion, and arranged to limit rearward movement of the shroud beyond second, rearward position in pre-use configuration.

13. An autoinjector as claimed in claim 12, wherein the syringe carrier includes a further latch element disposed rearwardly of the first-mentioned latch element, and arranged to cooperate with the latch element on the body portion to limit or prevent retraction of the shroud after having extended at the end of an injection.

14. The autoinjector device of claim 1,
wherein the syringe includes a barrel and a piston disposed within the barrel, wherein the piston is moveable between a rearward position and a forward position to urge the medicament from a forward end of the syringe; and the delivery mechanism arranged to act upon a plunger which includes or acts against the piston, and wherein the body portion comprises a window or viewing aperture extending along a longitudinal section of the syringe barrel through which the contents of the syringe may be inspected in use, the window or aperture being divided into forward and rearward portions, the forward portion being substantially aligned with the position of the piston at a forward end of the syringe when the delivery of the medicament is complete.

15. An injection device as claimed in claim 14, wherein the window or viewing aperture is divided by a transverse member.

16. An injection device as claimed in claim 15, wherein the syringe carrier includes at least two viewing apertures separated by a transverse member.

\* \* \* \* \*